(12) United States Patent
Bammer et al.

(10) Patent No.: US 11,000,342 B2
(45) Date of Patent: May 11, 2021

(54) DEVICES AND METHODS FOR TRACKABLE HEARING PROTECTION IN MAGNETIC RESONANCE IMAGING

(71) Applicant: The Board of Trustees of the Leland Stanford Junior University, Palo Alto, CA (US)

(72) Inventors: Roland Bammer, Palo Alto, CA (US); Julian Maclaren, Menlo Park, CA (US); Murat Aksoy, Menlo Park, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 533 days.

(21) Appl. No.: 15/134,795

(22) Filed: Apr. 21, 2016

(65) Prior Publication Data

US 2016/0310229 A1    Oct. 27, 2016

Related U.S. Application Data

(60) Provisional application No. 62/150,540, filed on Apr. 21, 2015.

(51) Int. Cl.
*A61B 90/00* (2016.01)
*A61B 5/055* (2006.01)
*A61B 5/11* (2006.01)

(52) U.S. Cl.
CPC .............. *A61B 90/39* (2016.02); *A61B 5/055* (2013.01); *A61B 5/1114* (2013.01); *A61B 5/1127* (2013.01); *A61B 2090/3954* (2016.02)

(58) Field of Classification Search
CPC ................................ A61B 90/39; A61B 34/20
See application file for complete search history.

(56) References Cited

U.S. PATENT DOCUMENTS

| | | | |
|---|---|---|---|
| 5,947,900 A * | 9/1999 | Derbyshire | G01R 33/5676 600/410 |
| 7,609,844 B2 | 10/2009 | Lederer | |
| 7,804,964 B2 | 9/2010 | Schreiber | |
| 8,214,012 B2 | 7/2012 | Zuccolotto et al. | |

(Continued)

OTHER PUBLICATIONS

Ooi, M. B., Krueger, S., Thomas, W. J., Swaminathan, S. V., & Brown, T. R. (2009). Prospective real-time correction for arbitrary head motion using active markers. Magnetic Resonance in Medicine: An Official Journal of the International Society for Magnetic Resonance in Medicine 62(4), 943-954. (Year: 2.*

(Continued)

*Primary Examiner* — Michael J Tsai
*Assistant Examiner* — Johnathan Maynard
(74) *Attorney, Agent, or Firm* — Lumen Patent Firm

(57) ABSTRACT

Hearing protection combined with head motion tracking for magnetic resonance (MR) procedures is provided. Trackable earplugs include an MR-visible sample combined with a passive resonant circuit. The trackable earplugs act as wireless markers for the MR system. A third wireless MR marker can be disposed on the forehead of the subject to facilitate motion tracking in six degrees of freedom (i.e., 3 rotations, 3 translations). Preferably, the coordinate system for motion tracking is rotated relative to standard MR coordinates to ensure distinct tracking peaks from the two trackable earplugs.

10 Claims, 10 Drawing Sheets

(56) References Cited

U.S. PATENT DOCUMENTS

| | | | |
|---|---|---|---|
| 2001/0020127 A1* | 9/2001 | Oshio | A61B 90/36 600/429 |
| 2004/0086138 A1* | 5/2004 | Kuth | A61F 11/08 381/72 |
| 2010/0210939 A1* | 8/2010 | Hartmann | A61B 17/1615 600/424 |
| 2014/0012127 A1* | 1/2014 | Biber | A61F 11/08 600/411 |
| 2014/0171784 A1 | 6/2014 | Ooi et al. | |
| 2015/0115956 A1 | 4/2015 | Ackerman et al. | |
| 2015/0382098 A1* | 12/2015 | Aita | H04R 1/1041 381/58 |
| 2016/0035108 A1* | 2/2016 | Yu | A61B 5/0077 382/131 |

OTHER PUBLICATIONS

Quick, H. H., Zenge, M. O., Kuehl, H., Kaiser, G., Aker, S., Massing, S., . . . & Ladd, M. E. (2005). Interventional magnetic resonance angiography with No. strings attached: wireless active catheter visualization. Magnetic Resonance in Medicine: An Official J of the International Society for Mag Res (Year: 2005).*

Ooi, M. B., Krueger, S., Thomas, W. J., Swaminathan, S. V., & Brown, T. R. (2009). Prospective real-time correction for arbitrary head motion using active markers. Magnetic Resonance in Medicine, 62(4), 943-954. (Year: 2009).*

Quick, H. H., Zenge, M. O., Kuehl, H., Kaiser, G., Aker, S., Massing, S., . . . & Ladd, M. E. (2005). Interventional magnetic resonance angiography with no strings attached: wireless active catheter visualization. Magnetic Resonance in Medicine, 53(2), 446-455. (Year: 2005).*

Duke University Hospital. (2014). Hearing Protection During MRI Exams. Duke University Health System. (Year: 2014).*

Derbyshire, J. A., Wright, G. A., Henkelman, R. M., & Hinks, R. S. (1998). Dynamic scan-plane tracking using MR position monitoring. Journal of magnetic resonance imaging, 8(4), 924-932. (Year: 1998).*

Burl, M., Courts, G. A., & Young, I. R. (1996). Tuned fiducial markers to identify body locations with minimal perturbation of tissue magnetization. Magnetic resonance in medicine, 36(3), 491-493. (Year: 1996).*

Flask, C., Elgort, D., Wong, E., Shankaranarayanan, A., Lewin, J., Wendt, M., & Duerk, J. L. (2001). A method for fast 3D tracking using tuned fiducial markers and a limited projection reconstruction FISP (LPR-FISP) sequence. Journal of Magnetic Resonance Imaging (Year: 2001).*

Busse, H., Trampel, R., Gründer, W., Moche, M., & Kahn, T. (2007). Method for automatic localization of MR-visible markers using morphological image processing and conventional pulse sequences: Feasibility for image-guided procedures. Journal of Magnetic Resonance Imaging, 26(4), 1087-1096. (Year: 2007).*

Krueger, S., Schaeffter, T., Weiss, S., Nehrke, K., Rozijn, T., & Boernert, P. (2006). Prospective intra-image compensation for non-periodic rigid body motion using active markers. In Proceedings of the 14th Annual Meeting of ISMRM (p. 3196). (Year: 2006).*

* cited by examiner

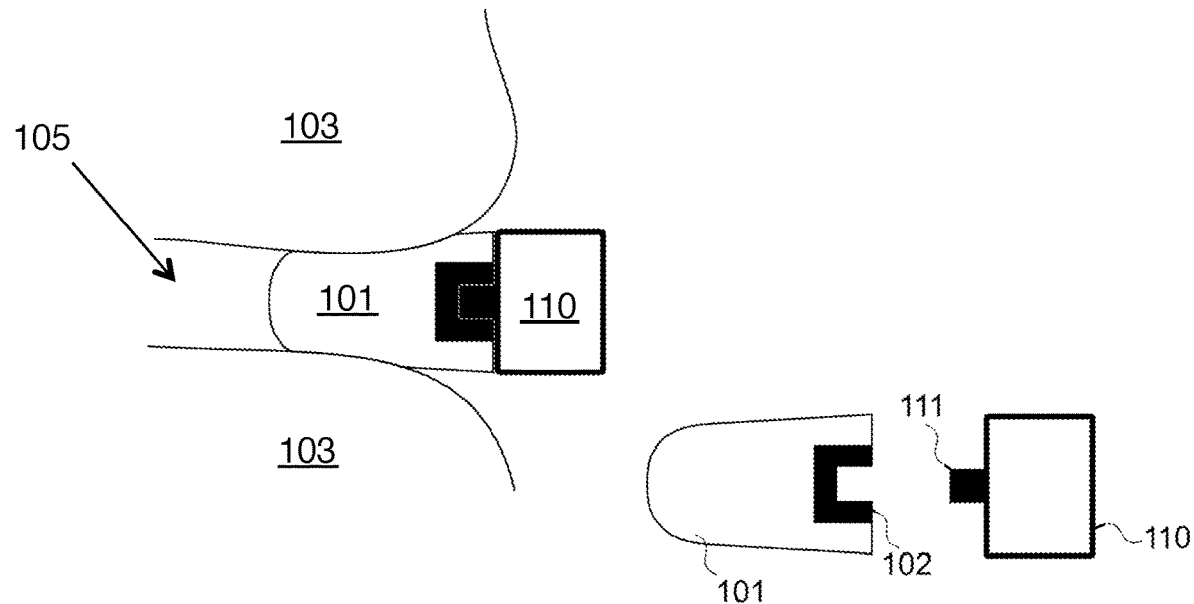
FIG. 1A
FIG. 1B
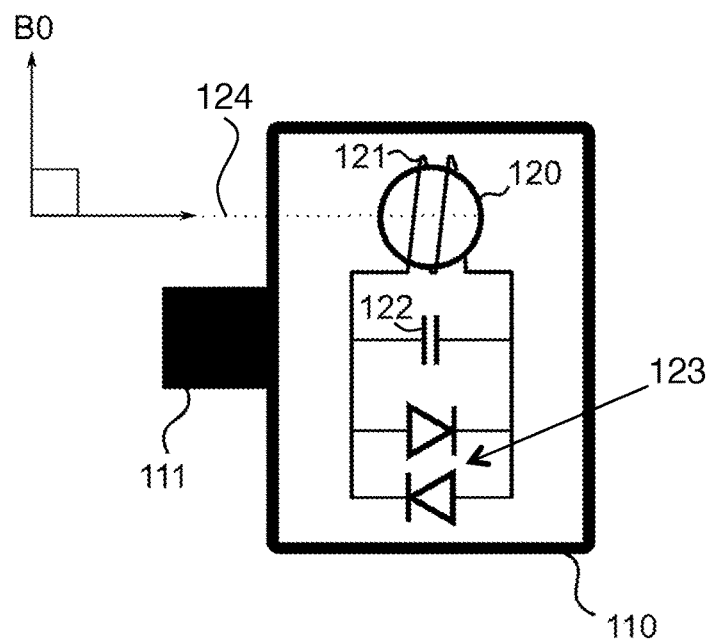
FIG. 1C

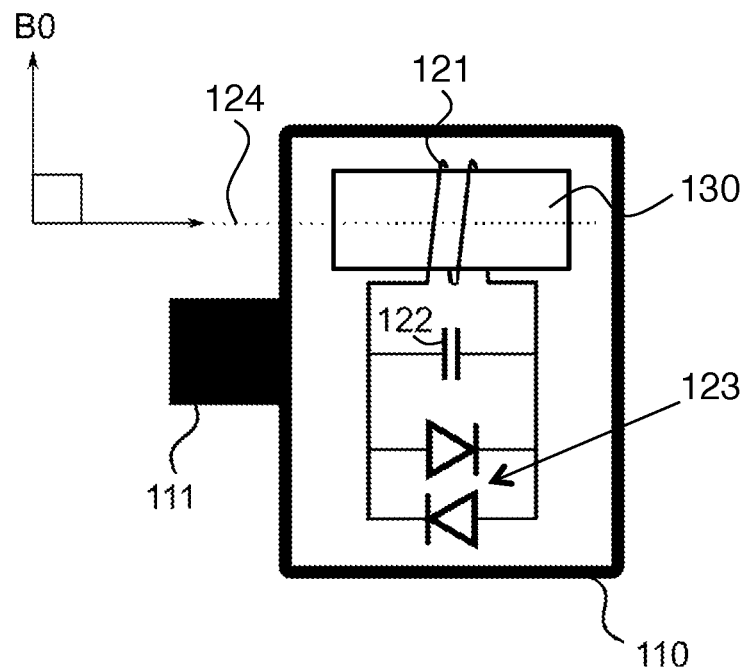
FIG. 1E
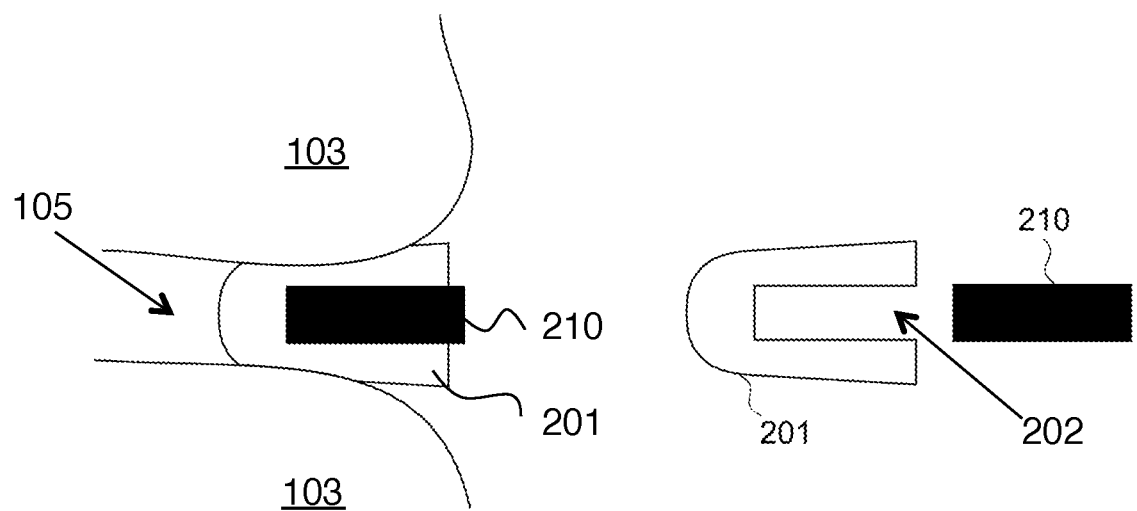
FIG. 2A
FIG. 2B

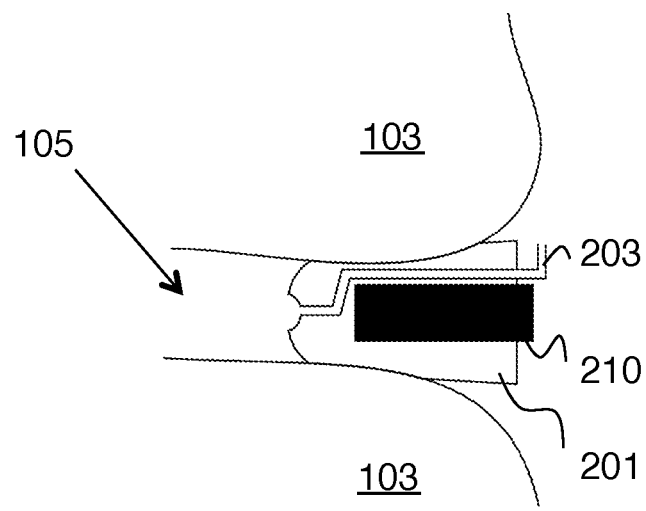
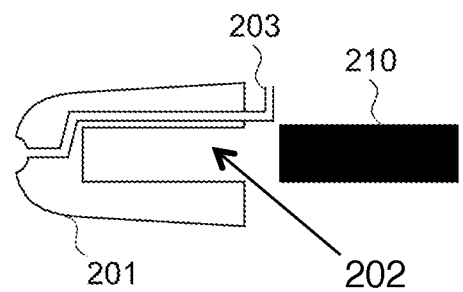
FIG. 2C
FIG. 2D
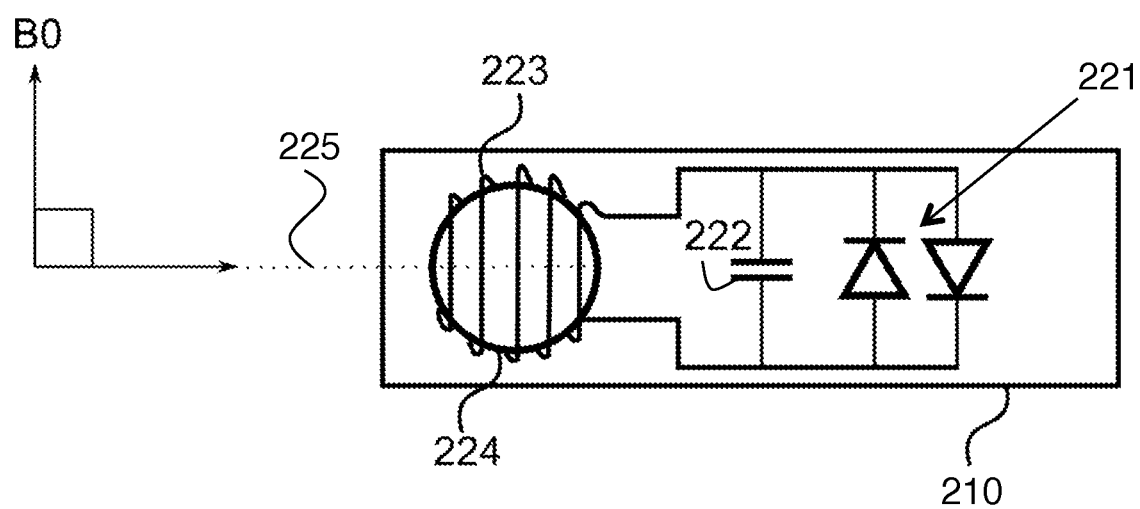
FIG. 2E

DEVICES AND METHODS FOR TRACKABLE HEARING PROTECTION IN MAGNETIC RESONANCE IMAGING

CROSS REFERENCE TO RELATED APPLICATIONS

This application claims the benefit of U.S. provisional patent application 62/150,540, filed on Apr. 21, 2015, and hereby incorporated by reference in its entirety.

GOVERNMENT SPONSORSHIP

This invention was made with Government support under contract EB011654 awarded by the National Institutes of Health. The Government has certain rights in the invention.

FIELD OF THE INVENTION

The present invention relates to motion tracking and hearing protection in magnetic resonance imaging.

BACKGROUND

Magnetic resonance imaging (MRI) is a valuable medical imaging technique, both for research and for clinical purposes. MRI is often used for imaging the human brain, largely due to its excellent soft tissue contrast and ability to generate images with many different contrasts. Magnetic resonance imaging of the brain is typically performed with the patient lying in a long narrow bore and with their head placed in a coil. The coil receives signal from tissue and, in some cases, transmits radiofrequency (RF) energy, in order to generate signal from the subject.

One challenge in MRI is the acoustic noise that is produced during a scan. The main source of this acoustic noise is the rapidly switching gradient fields in the strong static (B0) field. At 3 T, the noise generated can exceed 125 dB. This can cause anxiety for the patient, temporary hearing loss, and potentially even permanent hearing damage. For these reasons, hearing protection must be worn for every subject undergoing an MRI scan at common clinical field strengths (e.g. 1.5 T and 3 T) and at the higher field strengths (e.g. 7 T) used in research. The hearing protection typically used includes foam earplugs and/or headphones. Earplugs generally provide a higher degree of noise attenuation than headphones; however, they require practice to insert correctly. If not inserted properly, they can become loose over time and are no longer effective.

Another challenge in MRI is that the duration of each scan is on the order of minutes, and a complete examination can require around an hour. Most patients have difficulty remaining perfectly still for this length of time. This is problematic, because even motion of a few millimeters or less results in artifacts in the reconstructed images. In many cases, scans must be repeated, and in some cases, the patient must return to repeat the entire exam. Additionally, there are many patient populations (e.g. young children) who are simply unable to hold still and, as a result, these patients are often sedated. The problem of head motion in MRI therefore incurs a large financial cost, a potential risk to the patient for adverse events relating to the sedative, and inconvenience and stress for the patient and their family. Finally, there is a risk of misdiagnosis through poor quality images, for example, due to lesions obscured by motion artifacts.

In U.S. Patent App. US 2014/0171784 ('Method for 3D motion tracking using inductively coupled microcoils', hereby incorporated by reference in its entirety), Ooi et al. describe a method for tracking head motion in real time using small coils referred to as 'wireless markers'. Given real-time knowledge of head motion, it is possible to adaptively update the MRI scanner to compensate for the motion as it occurs. This general technique is known to those in the field as 'prospective' or 'adaptive' motion correction. Ooi et al. teach that in order to track head motion in the required six degrees of freedom (three translations, three rotations), three wireless markers are required. The three markers must all be attached to the same rigid body and arranged non-collinearly (collinear markers cannot measure rotations around the line that intersects them all). For these reasons, Ooi et al. use a pair of glasses to hold three markers at pre-defined locations. The glasses are worn by the subject during their MRI scan.

A key challenge of the approach described by Ooi et al. is that motion of the glasses is assumed to be equivalent to motion of the head of the subject. While this is often true, there are many head coils that fit extremely closely to the head of the subject. In these situations, it is possible for the glasses to physically contact the head coil and then move relative to the head. This can lead to erroneous motion tracking estimates. In addition, the requirement to wear glasses makes the subject's head larger and thus may not allow some patients to fit in the head coil.

From the above, it is clear that there is a need to both (a) obtain real-time head motion information in cases with a highly enclosed head coil and (b) to monitor hearing protection systems to ensure that they are functioning as intended. Accordingly, it would be an advance in the art to address these issues.

SUMMARY

This work addresses both of these challenges conveniently at the same time. Rather than mounting wireless markers on a separate physical body (e.g., glasses), the human body itself becomes the scaffold on which the wireless markers are attached to. These advancements both improve the practical applicability of the Ooi method and enable several other applications. In particular, this work addresses the two needs discussed above: it allows real-time motion information to be obtained in a tightly constrained space and simultaneously monitors the subject's hearing protection to ensure it is still correctly positioned. While this work is particularly applicable for use in human subjects undergoing MRI, aspects of this work will have application to animal imaging in some cases.

In a preferred embodiment, wireless markers are integrated into earplugs worn by the subject. In this embodiment, each earplug includes two parts: a disposable part which can be a modified foam earplug, designed to closely fit into the ear canal and attenuate noise; and a reusable wireless marker part, which attaches to the foam earplug. We refer to the combined unit of both parts as a 'trackable earplug'. In this preferred embodiment, the foam part of the trackable earplug has a cylindrical hole, in which the wireless marker part can be inserted.

In a preferred embodiment, the wireless marker is completely encased in a cylinder of epoxy or plastic. It can therefore be sterilized using the alcohol solutions typically used for cleaning foam padding and other items that come into contact with a patient's skin during an MRI exam. In this preferred embodiment, the components of the active marker include an MR-visible sample, a coil wound around the MR-visible sample, a capacitor used for forming a resonant circuit, tuned to the resonance frequency of the sample, and a pair of crossed diodes to limit the voltage across the coil and hence the current flowing through it. In a preferred embodiment, the sample is spherical with a radius of 1 mm or less. The coil is preferably wound as close as possible to the sample, so that it both supports the sample and requires as little space as possible within the wireless marker unit. Ideally, the coil is arranged so that when inserted into the foam earplug to form the trackable marker, it lies as far into the ear canal as possible. In this way it moves rigidly with the head motion of the subject.

In another embodiment, the earplug is made of a two-component moldable paste. When both components of the paste are combined, it hardens within a few minutes. During the hardening period, the moldable paste conforms snugly to the ear and allows one to insert a microcoil in each ear.

In a preferred embodiment, all wireless markers are aligned so that the axis that passes through the coil within the wireless marker lies perpendicular to the B0 direction of the MR scanner during normal operation. Thus the coil axis is defined as being perpendicular to a loop (or loops) of the coil, such that the loop(s) of the coil wind around the axis of the coil. Here, we refer to this as the 'coil orientation condition'. The coil orientation condition ensures that the maximum possible signal is obtained from the coil of the wireless markers. In this preferred embodiment, wireless markers can be manufactured with a small protruding 'stem' to indicate the preferred orientation. Preferably this coil orientation condition is satisfied to within +/−45 degrees. More preferably the coil orientation condition is satisfied to within +/−10 degrees.

BRIEF DESCRIPTION OF THE DRAWINGS

FIGS. 1A-B shows an earplug suitable for insertion in the ear canal of a subject, with an integrated connection mechanism allowing a wireless marker to be securely attached to it.

FIG. 1C shows a more detailed view of the wireless marker in FIGS. 1A-B.

FIG. 1E shows a wireless marker including a rod-shaped MR-visible sample.

FIG. 2A-B show a more compact version of the device in FIG. 1A, where the wireless marker is encased in epoxy and inserted into the earplug.

FIGS. 2C-D show a modification to the trackable earplugs shown in FIGS. 2A-B, where a tube allows delivery of acoustic stimuli for functional MRI through the earplugs.

FIG. 2E shows a more detailed view of the wireless marker design of FIGS. 2A-D.

DETAILED DESCRIPTION

Figure 1D:
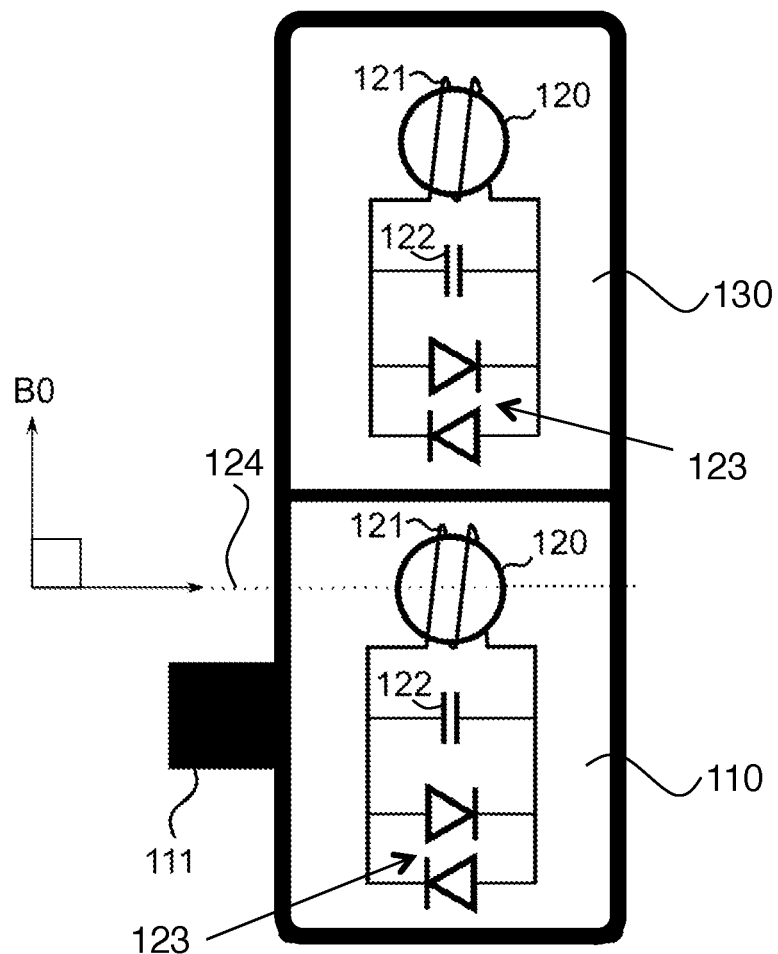
FIG. 1D shows a wireless marker including two MR-visible samples.

FIGS. 1A-B show an earplug 101 suitable for insertion in the ear canal 105 of a subject 103. The earplug includes a plastic insert 102 with a centered hole, which acts as a connecting mechanism. This allows a wireless marker 110 to be securely attached to it by inserting the matching connecting mechanism 111 on the wireless marker unit into the earplug. The combined 'trackable earplug', including an earplug and wireless marker, can be assembled either before or after insertion of the foam portion into the ear canal. The earplug material preferably provides acoustic noise attenuation of at least 30 dB. The wireless marker allows the position of the trackable earplug to be obtained in three degrees of freedom within the imaging volume of the MRI scanner, when used according to the methods described here.

FIG. 1C provides a more detailed view of the internal components of the wireless marker shown in FIG. 1A. The plastic shell of the wireless marker 110 includes a connector 111 enabling it to be easily attached to the earplug. The earplug itself is preferably disposable, and this connecting mechanism allows the wireless marker to be removed from the earplug using the connector and reused. The wireless marker 110 contains a MR-visible sample 120, which can be spherical as shown. The MR-visible sample 120 is surrounded by a coil 121, which serves to receive signal from the sample. Although coil 121 is shown here as having multiple loops, it is also possible for coil 121 to have a single loop. A resonant circuit is constructed from the coil 121 and a capacitor 122, and the resonant circuit is tuned to the known resonance frequency of the sample. Two crossed diodes 123 connected in parallel are also included to limit the voltage across the coil, particularly during RF transmit for protection. Our experiments indicate that the crossed diodes are useful to prevent heating during imaging with RF-intensive sequences. Importantly, the coil 121 is arranged so that when inserted into the ear canal of a subject lying in an MRI scanner, the axis 124 of the coil is perpendicular to the direction of the scanner B0 field. Here we refer to this as the 'coil orientation condition'. This means that the axis that passes through the coil is parallel to the long axis of the earplug. This ensures when the earplugs are inserted into the ear canal, the coil orientation condition holds.

Although the ear canal does not lie perfectly perpendicular to the B0 field direction (i.e., the head to foot direction) for most subjects, the approximation is sufficient to adequately fulfill the coil orientation condition. Slightly tilting the coil axis orientation relative to the longitudinal axis of the earplug to counteract the angle of the ear canal is counterproductive: the earplug is best made rotationally symmetric, such that the subject and scanner operator cannot inadvertently rotate it to an incorrect orientation and potentially violate the coil orientation condition. The coil orientation condition is particularly important for the third wireless marker, since there is no 'ear canal axis' to guide placement. Instead, when the third wireless marker is placed on the forehead, the coil axis preferably points in the subject's left-right direction or the subject's anterior-posterior direction. In either case, the coil axis ends up being perpendicular to the B0 magnetic field of the MR system, as desired.

In a preferred embodiment, the MR-visible sample 120 contains water doped using standard MRI contrast agents to reduce the relaxation times T1 and T2 to values below that normally found in human soft tissue. The reason for doping the sample is to prevent the active marker component of the trackable earplugs from being visible in the MR images during imaging. Our research has shown that if the sample is not sufficiently doped, then signal from previous excitation can remain in the sample and propagate into nearby MRI imaging slices. This can be avoided if the relaxation times T1 and T2 are sufficiently short, because then signal does not remain for long enough to be detectable in any MRI sequence apart from the MRI navigator tracking sequence that is specifically designed to track the wireless markers. In another embodiment, the tracking sequence used is a variant of ultrashort echo time (UTE) imaging. In this embodiment, the markers are doped such that their T2 relaxation time is less than 1 ms.

In another embodiment, the wireless markers also include a resistor, or resistive wire. This reduces the Q factor of the resonant circuit, which also reduces the likelihood of the markers being visible in a regular imaging sequence. A lower Q factor also reduces sensitivity to small mismatches between the resonant frequency of the circuit and the proton resonant frequency.

One embodiment of the invention is a device for tracking the head of a living subject in a magnetic resonance (MR) system. Here MR system includes both MR imaging systems and MR spectroscopy systems where MR data other than imaging data is collected. The device includes two earplugs, where each earplug includes an integrated MR-visible wireless marker. Each wireless marker includes: a) an MR-visible sample having a sample resonant frequency, and b) a coil disposed around the MR-visible sample. Here the coil has a coil resonant frequency that is tuned to the sample resonant frequency, and as indicated above it is convenient to define the axis of the coil as being perpendicular to loop(s) of the coil.

Two or more wireless markers can be included in the trackable earplug. FIG. 1D shows a preferred configuration for this. In this example, each trackable earplug contains two wireless markers 110 and 130 integrated with each other such that the axis connecting each pair of wireless markers is perpendicular to the axis 124 connecting the left and right trackable earplugs. This configuration allows complementary projection data and allows determination of rotational motion of the head around the axis connecting the left and right trackable earplugs (i.e., axis 124). In this embodiment, the wireless marker on the forehead is not needed to get six-degree-of-freedom head motion information.

In another embodiment, each wireless marker contains a sample that is not spherical, but has some other shape. FIG. 1E shows an example where the MR-visible sample 130 is rod-shaped. In this case, it is possible to obtain rotation information by analyzing the shape of each projection. This means that it is possible to obtain six-degree-of-freedom head motion information with fewer than three markers.

In another embodiment, each wireless marker is not identical, but rather differs from the others in a unique way. One such embodiment is when MR visible beads, or spherical samples, of different sizes are used. That way, the peak width differs for each wireless marker, allowing them to be uniquely identified. Another such embodiment is when multiple MR visible beads, or spherical samples, are included within each wireless marker. In this case, multiple peaks appear in close proximity, forming a 'peak cluster'. The number of peaks in each 'peak cluster' can be used to uniquely identify each wireless marker.

In another embodiment, foam earplugs are equipped with small optically visible samples, such as reflective spheres. The position of each reflective sphere can be monitored using a camera to obtain motion information from the subject. If the reflective spheres are used in conjunction with wireless markers, then the relative location of the two marker types can be found using a cross-calibration procedure.

FIGS. 2A-B show a more compact design of the trackable earplug shown in FIGS. 1A-B. In this design, the earplug 201 contains a cylindrical hole 202 designed to fit over a miniaturized wireless marker 210 in the form of a cylindrical plug. FIGS. 2C-D show that the trackable earplugs of FIGS. 2A-B can be manufactured to contain a small tube 203 with internal diameter of ~1 mm, so that acoustic stimuli can be delivered to the subject through the trackable earplugs. The approach of FIGS. 2C-D is an alternative to wearing pneumatic headphones and is particularly useful for fMRI (functional MRI) applications within enclosed head coils. Acoustic fMRI stimuli can then be delivered to the subject through the trackable earplugs, without the need for large external headphones.

FIG. 2E shows how the components of the wireless marker can be arranged so that they can be formed into a cylindrical plug made of epoxy. The coil 223 is preferably arranged so that it serves as a sample holder for the MR-visible sample 224. Although coil 223 is shown here as having multiple loops, it is also possible for coil 223 to have a single loop. The tuning capacitor 222 and crossed diodes 221 are placed further along the cylindrical plug, so as to minimize the diameter of the plug. As in the design shown in FIG. 1C, the coil 223 is arranged so that when inserted into the ear canal of a subject lying in an MRI scanner, the axis 225 of the coil is perpendicular to the direction of the scanner B0 field.

Figure 3A:
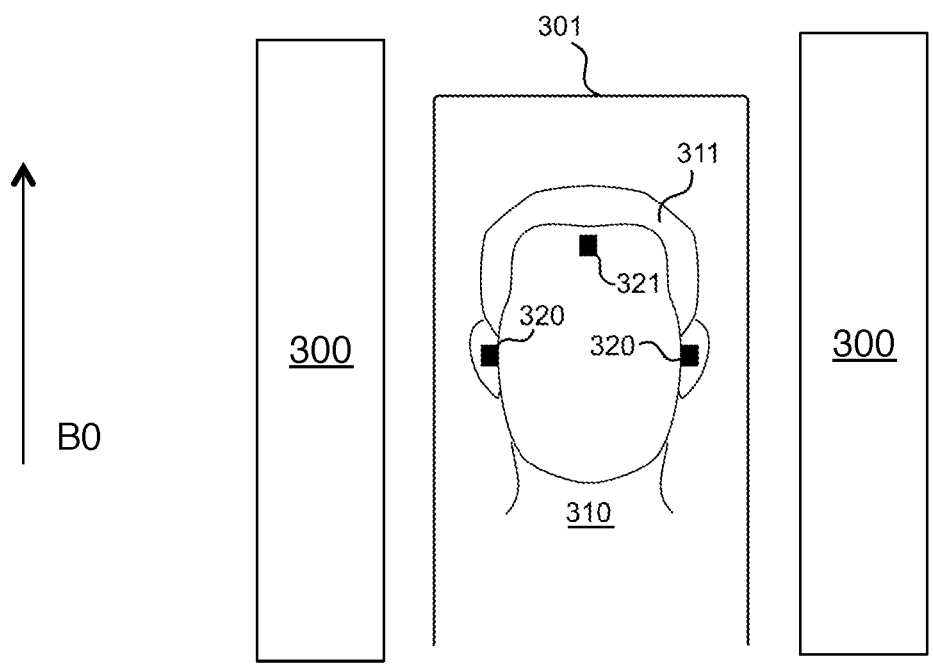
FIG. 3A shows how two trackable earplugs, and an extra wireless marker worn on the forehead, can be attached to the subject during a magnetic resonance imaging exam.

FIG. 3A shows how two trackable earplugs 320, and a third wireless marker 321, can be attached to the subject 310 during a magnetic resonance imaging exam. Here the subject wears another wireless marker 321, which can be placed on their forehead anywhere between the bridge of their nose and their hairline (or somewhere else on the head that allows sufficient separation of signals from the remaining two microcoils). This third wireless marker is not integrated into a trackable earplug; however, it is otherwise identical to the wireless markers used within the trackable earplugs.

Figure 3B:
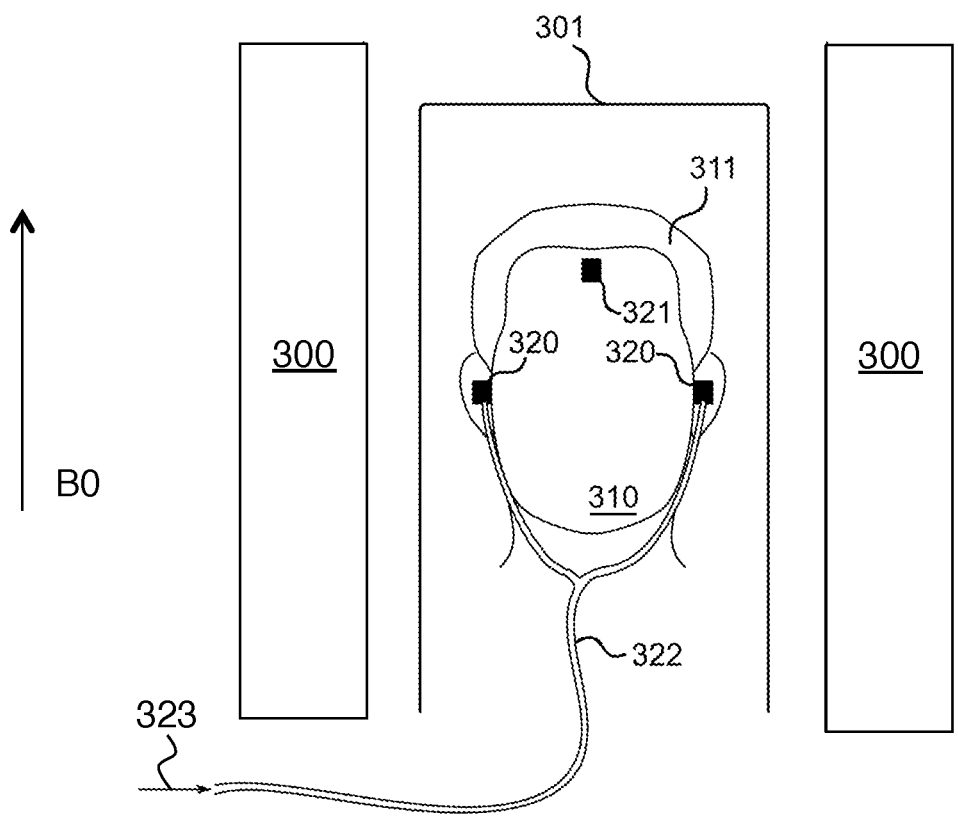
FIG. 3B shows how the system in FIG. 3A can be used with a pneumatic tube to deliver audio to the subject.

The third wireless marker 321 enables tracking of the subject's head motion in six degrees of freedom, when the methods described here are applied. The third wireless marker 321 (which can be potted) is attached to the forehead. It is not attached to the hair of the subject 311, since hair typically moves relative to the subject's head in an unpredictable fashion. When the subject 310 is placed on the patient table 301 in an MRI scanner 300, the orientation of the axes of the coils in the wireless markers all lie perpendicular to the direction of the B0 field. FIG. 3B shows how the setup in FIG. 3A can be used to deliver acoustic stimuli (or other audio signals) 323 to the subject using a tube 322. In the example in FIG. 3B, the earplugs used are those shown in FIGS. 2C-D, i.e., they contain a small tube that penetrates the earplug.

Figure 4:
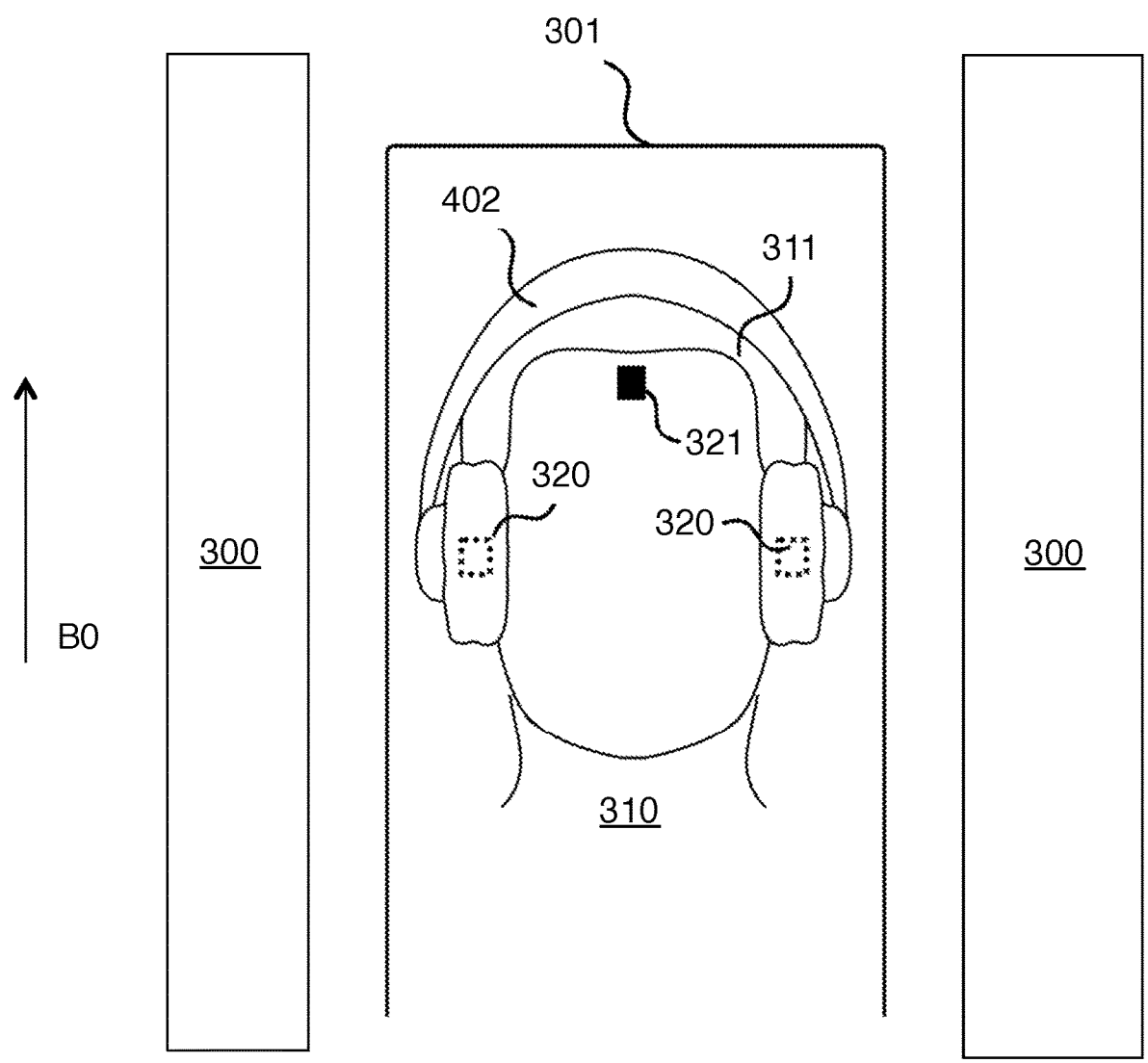
FIG. 4 shows how regular headphones can be worn by the subject in addition to the three wireless markers.

FIG. 4 shows how the setup in FIGS. 3A-B is compatible with standard MRI-compatible headphones 402. In this case, the subject 310 lies on the patient table 301 inside the MRI scanner 300 and wears two trackable earplugs 320. If motion tracking in six degrees of freedom is required, then an extra wireless marker 321 is attached to the skin on the forehead below the subject's hair 311. The subject 310 wears headphones 402 over the top of the trackable earplugs 320. The earplugs are sufficiently deep in the ear canals of the subject that there is no physical contact between the headphones and the trackable earplugs. Likewise, there is no physical contact between the headphones and the extra wireless marker attached to the forehead. It is important that the headphones do not contact either marker type, since the headphones may move with respect to the head and if such motion is transferred to the markers, head-tracking quality is affected. Thus the headphones do not interfere with the operation of the trackable earplugs or third wireless marker attached to the forehead. The use of headphones as shown in FIG. 4, reduces the minimum allowable acoustic attenuation requirement of the trackable earplugs. In addition, headphones provide the ability to listen to audio, including instructions from the scanner operator.

An exemplary embodiment is a method for tracking the head of a living subject in a magnetic resonance (MR) system. Here also, MR system includes both MR imaging systems and MR spectroscopy systems where MR data other than imaging data is collected. The method includes a) providing two trackable earplugs where each earplug includes an integrated MR-visible earplug wireless marker. Each earplug wireless marker includes an MR-visible sample having a sample resonant frequency, and a coil disposed around the MR-visible sample. Here the coil has a coil resonant frequency that is tuned to the sample resonant frequency. The axis of the coil is defined to be perpendicular to loop(s) of the coil.

b) disposing the earplugs in ear canals of the subject; and c) tracking positions of the earplug wireless markers by obtaining projections from one or more localization gradients in an MR pulse sequence.

Variations of this basic method mainly relate to a) further aspects of motion correction, b) the coordinates used for tracking, and c) marker distance monitoring. These topics are considered in turn below.

As described above, use of a third wireless marker (e.g., disposed on the forehead of the subject) combined with position tracking of the earplug wireless markers and the third wireless marker provides head motion tracking for three orthogonal translations and three orthogonal rotations (i.e., six degrees of freedom).

Performing motion correction based on the tracking positions of the earplug wireless markers and of the third wireless marker can be done. This motion correction can be applied retrospectively, but in this preferred embodiment motion correction is applied adaptively. Such motion correction can be applied adaptively to MR imaging by updating encoding magnetic fields of the MR system in real time. The adaptive motion correction procedure is described in Ooi et al. and its application to imaging is known well to those skilled in the art. Such motion correction can also be applied adaptively to a navigator sequence for MR tracking, whereby improved tracking can be provided (e.g., preventing overlap of the peaks in the projections of the wireless markers, even under extreme rotation).

In another embodiment, the trackable earplugs are used during a PET-MR (positron emission tomography-MR) examination. The motion tracking data is then used to correct the PET data after acquisition. Similarly, motion tracking using MR-visible earplugs can be used to provide motion correction for any non-MRI medical imaging modality in cases where the non-MR medical imaging modality is performed in combination with MR motion tracking (and optionally MR imaging). Here the motion correction is applied to the data obtained from the non-MR medical imaging modality.

Figure 5:
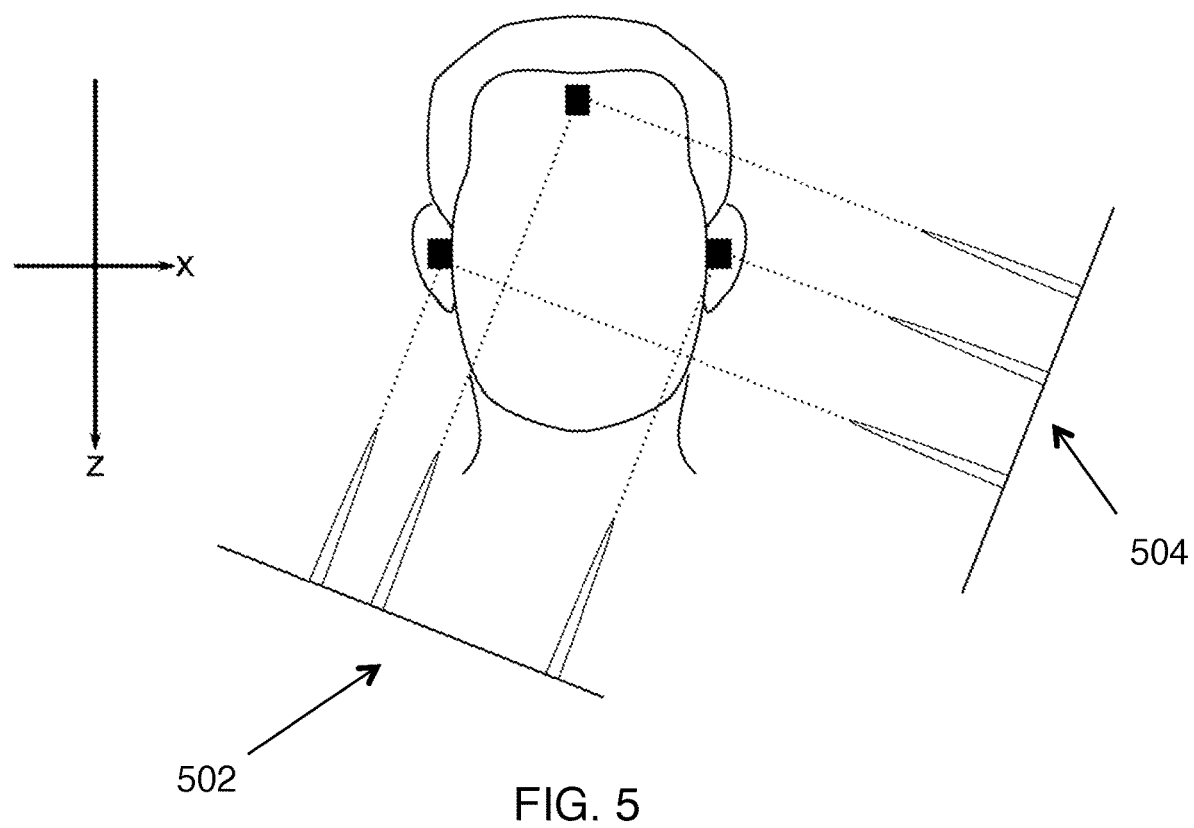
FIG. 5 shows how a mixture of gradient axes is used to obtain projections from the wireless markers where the projection peaks are non-overlapping.
Figures 6A, 6B:
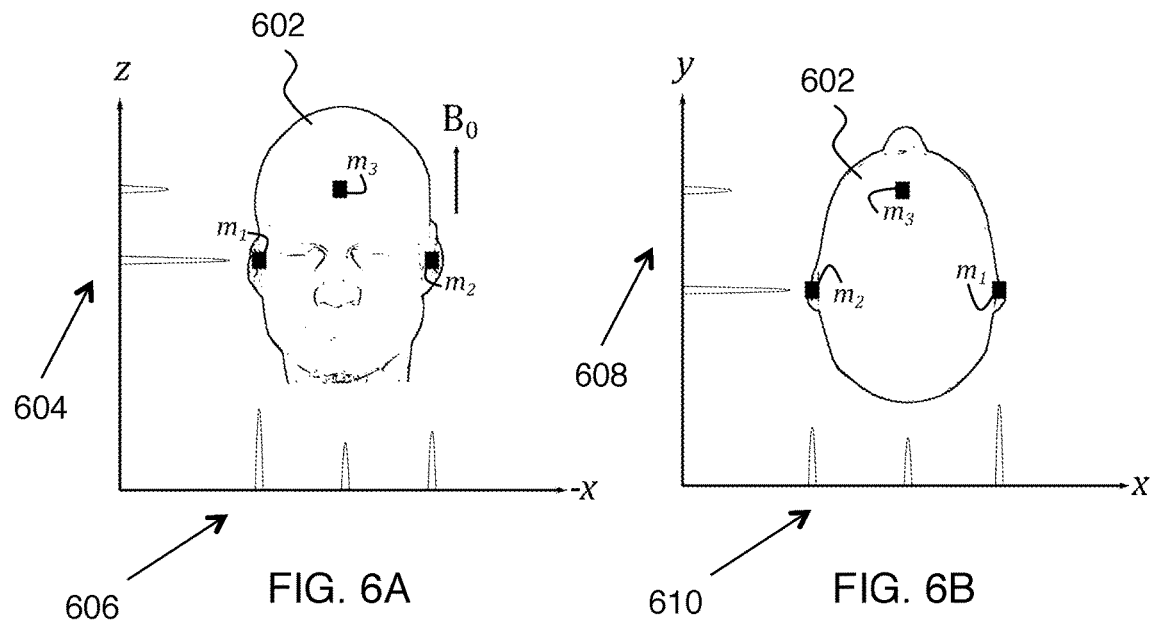
FIGS. 6A-D show in more detail how peaks can overlap if the regular x, y and z gradients are used to provide the projections and how this can be avoided by using a mixture of gradients.
Figures 6C, 6D:
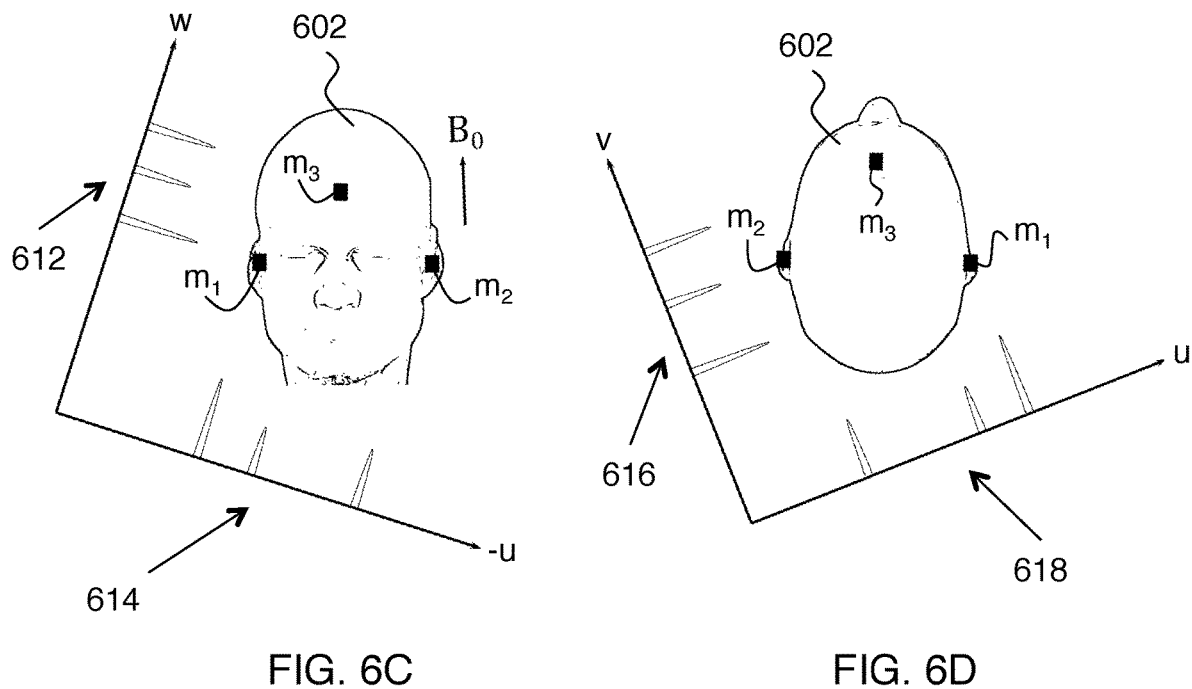

FIG. 5 shows a two-dimensional example illustrating how a combination of gradient axes is used to obtain projections from the wireless markers, such that the projection peaks do not overlap. In this example, the method taught by Ooi et al. in US 2014/0171784 is insufficient because a projection on the physical z-axis only shows two peaks. This coincidence of the peaks is because both trackable earplugs have the same z coordinate. By using a combination of gradients to obtain projections, peaks can be sufficiently separated from each other, e.g., as in projections 502 and 504 on FIG. 5.

For clarity, the same concept is illustrated in three dimensions in FIGS. 6A-D. If projections 604, 606, 608 and 610 are acquired using an x-y-z coordinate system (where x, y and z correspond to the physical gradient axes x, y and z, respectively) they would be insufficient to obtain unique peaks from markers $m_1$, $m_2$, $m_3$, due to the geometry of the head 602 in the MRI scanner and the arrangement of the markers. Instead, a u-v-w coordinate system is used for marker tracking, which is a rotated version of the x-y-z coordinate system. Here it is apparent that projections 612, 614, 616 and 618 in the u-v-w coordinates provide separate peaks for markers $m_1$, $m_2$, $m_3$ in three dimensions.

The rotation matrix required to give the location of a point in scanner physical x-y-z coordinates from its location in u-v-w coordinates is referred to as R. The rotation matrix R is known and preferably predefined before the beginning of the MRI examination. In fact, since the geometry of the head of each human subject is similar, in our preferred implementation, R is preferably constant for all subjects.

In the example of FIGS. 6A-D, the x-y-z standard MR coordinates shown are for a subject lying on his or her back. For a subject lying on his or her side, the x and y directions of the standard MR coordinates are exchanged relative to what is shown. This does not significantly affect the above-described coordinate rotations to obtain distinct peaks from the trackable earplugs. In either case, gradient coordinates of the localization gradients are rotated with respect to standard coordinates of the MR system such that peaks from the wireless markers are non-overlapping for three or more projections.

In a preferred embodiment, three projections are applied using the MRI scanner to detect the locations of each wireless marker. Importantly, these projections are preferably applied using a mixture of the physical scanner gradients. This is done, because as described above, three projections applied using the x, y and z gradients individually are not sufficient to uniquely identify the locations of the three markers when arranged as described. In this embodiment, the mixture of gradients is selected so that the new coordinate axes form an orthogonal coordinate system (where the coordinate surfaces all meet at right angles) and the three wireless markers form distinctly separate peaks when projected onto each of these three axes.

In a preferred embodiment, the locations of the peaks corresponding to each marker are identified, giving the location of each marker in u, v, w coordinates. The location of each marker is then determined in x-y-z coordinates by multiplication with matrix R. Using methods well known to workers in this field, the set of three points corresponding to the wireless marker locations in scanner x-y-z coordinates can then be used to give motion information in six degrees of freedom. In another equivalent embodiment, this motion information is directly calculated in u, v, w coordinates and then converted to physical scanner coordinates using rotation matrix R.

In another embodiment, the axes u, v, w form a skew (i.e., non-orthogonal) coordinate system, rather than a orthogonal coordinate system. This can help to ensure optimal peak spacing in the marker projections.

In another embodiment, more than three projections are applied to localize the markers. In this embodiment, any projections that contain fewer than the expected number of peaks are discarded. The marker location can then be found using a number of techniques known to those in the field, such as backprojection methods or by solving a linear system of equations, where the unknowns are the marker coordinates.

Figure 7:
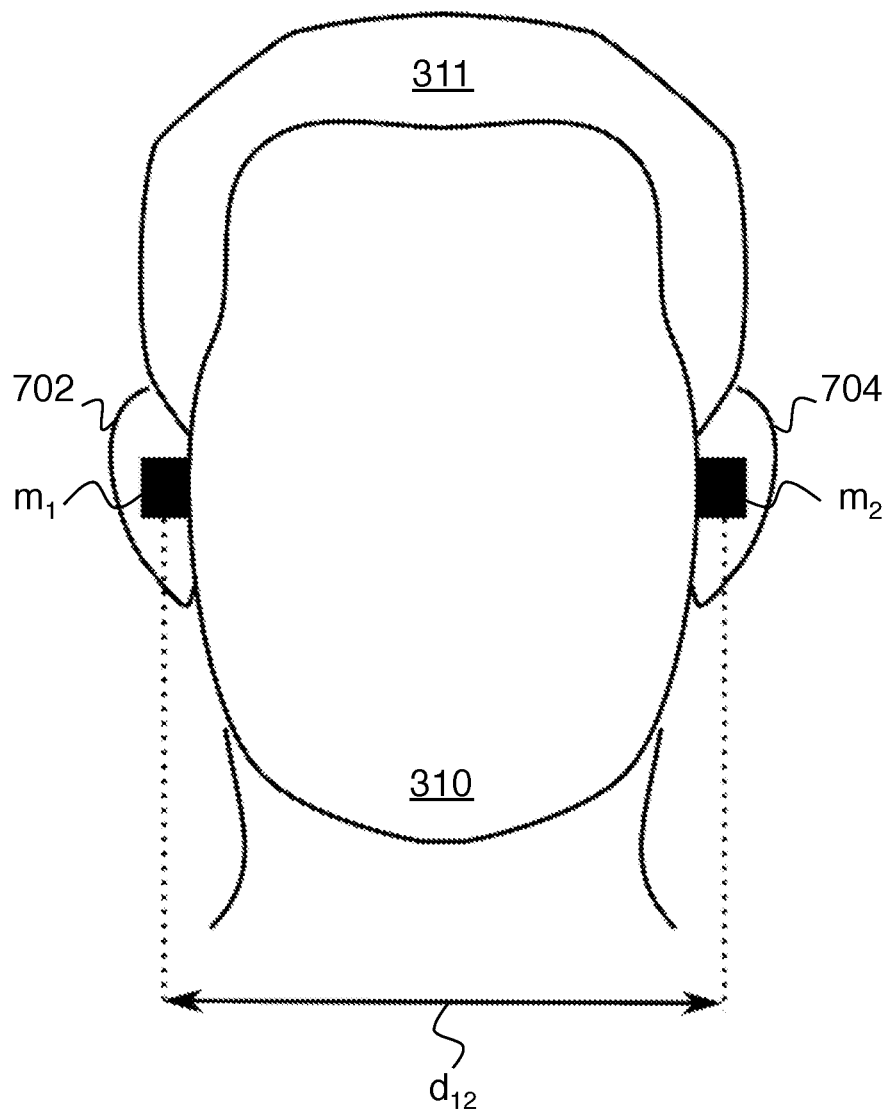
FIG. 7 shows how the distance between the two earplugs may be defined.

FIG. 7 shows how the Euclidean distance $d_{12}$ can be defined between two wireless markers, labeled here as $m_1$ and $m_2$. More specifically, if marker $m_1$ has coordinates $(x_1(t), y_1(t), z_1(t))$ and marker $m_2$ has coordinates $(x_2(t), y_2(t), z_2(t))$, then the Euclidean distance is given by $$d_{12}(t) = \sqrt{(x_1(t) - x_2(t))^2 + (y_1(t) - y_2(t))^2 + (z_1(t) - z_2(t))^2}.$$

Here all coordinates are shown with a time dependence to account for possible motion of the earplugs after insertion. In this example, the Euclidean distance between two trackable earplugs worn by the subject in ears 702 and 704 is calculated. Monitoring this distance provides a great deal of useful information, specifically whether or not the subject is, in fact, wearing earplugs and whether the earplugs have moved at all since the first time this measurement was made.

In a preferred embodiment, the relative displacement between the two trackable earplugs is monitored during the MRI exam. If the displacement changes by more than a certain threshold (for example, by more than 1 mm along any axis), this indicates that one, or both, of the trackable earplugs has moved relative to the subject's ear canal. This indicates that the earplug may no longer be providing acceptable acoustic noise attenuation, because even a small air gap between the foam of the earplug and the internal surface of the ear canal severely compromises attenuation. The relative positional change information can be also used to monitor the third microcoil. In this preferred embodiment, the scan can be automatically stopped if such a situation arises. Similarly, in this preferred embodiment, if an earplug is not detected, the scan can be immediately and automatically stopped.

Figure 8:
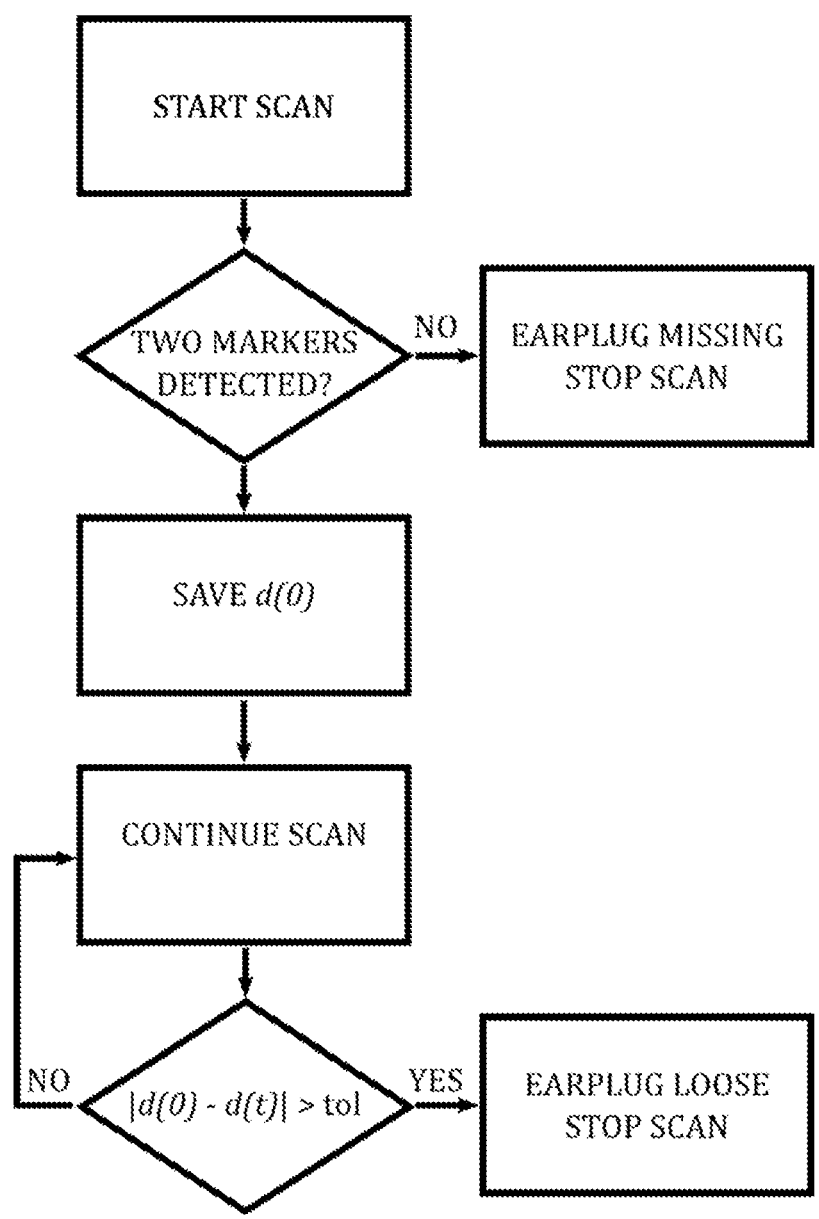
FIG. 8 is a flowchart describing an algorithm that can be used to stop a scan if an earplug is missing or comes loose.

An exemplary algorithm for distance monitoring is summarized by the flowchart shown in FIG. 8. After starting the scan, the navigator sequence is played out on the scanner. Since, in this example, the subject is wearing two trackable earplugs, it is expected that two wireless markers will be located by the navigator. If this is not the case, it is likely that one of the earplugs is missing (i.e. it may have fallen out prior to starting the scan, or the technologist or subject may have forgotten to insert it). In this case, the scan is stopped, so that the situation can be corrected. If, on the other hand, two markers are detected, then the Euclidean distance at the time of starting the scan, denoted d(0), is calculated. The scan continues and the trackable earplug locations are periodically re-measured and the distance, d(t), is calculated. If at any time the absolute difference between the latest distance, d(t), and the initially measured distance d(0), exceeds a threshold, then the scan is stopped, because this indicates that one of the trackable earplugs has become loose or fallen out completely. In this manner, it can be ensured that the subject is always wearing suitable hearing protection.

The invention claimed is:

1. A method for tracking the head of a living subject in a magnetic resonance (MR) system, wherein the method comprises:
   a) providing two earplugs, wherein each earplug comprises an integrated MR-visible earplug wireless marker;
   wherein each earplug wireless marker comprises
   an MR-visible sample having a sample resonant frequency, and
   a coil disposed around the MR-visible sample;
   wherein the coil has a coil resonant frequency that is tuned to the sample resonant frequency,
   wherein an axis of the coil is perpendicular to a loop of the coil;
   b) disposing the earplugs in ear canals of the subject;
   c) tracking positions of the earplug wireless markers by obtaining projections from one or more localization gradients in an MR pulse sequence;
   further comprising monitoring a distance between the earplug wireless markers as determined from the tracking positions of the earplug wireless markers, whereby changes in earplug wireless marker position relative to the head of the subject during an MR procedure can be detected;
   further comprising determining whether or not the earplugs have moved from their initial positions during the MR procedure from the monitoring the distance between the earplug wireless markers;
   wherein the distance between the earplug wireless markers is monitored with sufficient accuracy to sense a distance change of 1 mm or more;
   further comprising comparing the monitored distance between the earplug wireless markers to an initial distance between the earplug wireless markers, and signaling a hearing protection fault if a difference between the monitored distance and the initial distance exceeds a predetermined threshold;
   further comprising automatically aborting the MR procedure if the hearing protection fault is signaled.

2. The method of claim 1, wherein gradient coordinates of the localization gradients are rotated with respect to standard coordinates of the MR system such that peaks from the wireless markers are non-overlapping for three or more projections.

3. The method of claim 1, further comprising:
   d) disposing a third wireless marker on the head of the subject;
   wherein the third wireless marker comprises
   an MR-visible sample having a sample resonant frequency, and
   a coil disposed around the MR-visible sample;
   wherein the coil has a coil resonant frequency that is tuned to the sample resonant frequency;
   e) tracking a position of the third wireless marker by obtaining projections from one or more localization gradients in an MR pulse sequence.

4. The method of claim 3, wherein position tracking of the earplug wireless markers and the third wireless marker provides head motion tracking for three orthogonal translations and three orthogonal rotations.

5. The method of claim 3, further comprising performing motion correction based on the tracking positions of the earplug wireless markers and of the third wireless marker.

6. The method of claim 5, wherein the motion correction is applied adaptively to MR imaging by updating encoding magnetic fields of the MR system in real time.

7. The method of claim 5, wherein the motion correction is applied adaptively to a navigator sequence for MR tracking, whereby improved tracking can be provided.

8. The method of claim 5, further comprising obtaining data from a non-MR medical imaging modality, wherein the motion correction is applied to the data obtained from the non-MR medical imaging modality.

9. The method of claim 1, wherein the MR-visible samples are non-spherical, whereby images of the MR-visible samples provide information on orientation of the wireless markers.

10. The method of claim 1, further comprising automatically aborting the MR procedure if two earplug wireless marker signals are not detected.

* * * * *